United States Patent [19]

Molnár et al.

[11] 4,395,568
[45] Jul. 26, 1983

[54] ANIONIC SURFACE ACTIVE AGENTS

[75] Inventors: Attila Molnár; György Csermely; György Lányi, all of Budapest, Hungary

[73] Assignee: Chinoin Gyogyszer es Vegyeszeti Termekek Gyara Rt., Budapest, Hungary

[21] Appl. No.: 199,315

[22] Filed: Oct. 21, 1980

[30] Foreign Application Priority Data

Oct. 26, 1979 [HU] Hungary .............................. CI 1980

[51] Int. Cl.³ ........................ C07C 69/34; C07C 69/52
[52] U.S. Cl. ..................................... 560/198; 560/85; 560/193; 252/174.21
[58] Field of Search ........................ 560/85, 193, 198

[56] References Cited

U.S. PATENT DOCUMENTS

| | | | |
|---|---|---|---|
| 2,626,928 | 7/1953 | De Groote | 560/85 |
| 2,679,518 | 5/1954 | De Groote | 560/85 |
| 3,968,310 | 7/1976 | Stowell | 560/193 |
| 4,154,958 | 5/1979 | Bollinger | 560/193 |

*Primary Examiner*—Paul J. Killos
*Attorney, Agent, or Firm*—Hubbell, Cohen, Stiefel & Gross

[57] ABSTRACT

Anionic surface active agents of the general formulae I and II

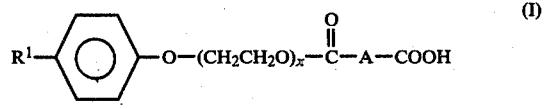

(I)

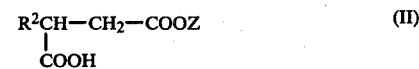

(II)

where
$R^1$ is $C_{1-12}$ alkyl;
A is $-(CH_2)_n-$ (wherein n is 0–6), $-CH=CH-$, phenylene, or alkylphenylene;
x is an integer of 3 to 35;
$R^2$ is $C_{8-12}$ alkyl or alkenyl;
Z is $-(CH_2CH_2O)_xH$ or

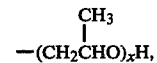

where x is as defined above;
and the salts thereof with inorganic or organic bases.

These surfactants have excellent surface active properties and hard water tolerance, and may be prepared by conventional esterification techniques.

2 Claims, No Drawings

ANIONIC SURFACE ACTIVE AGENTS

This invention relates to anionic surface active agents containing a primary or secondary carboxyl group, and their production.

As is known, anionic surfactants containing a carboxyl group have only limited applicability in hard water. Their calcium and magnesium salts are mostly water insoluble and precipitate out from aqueous solutions. Simultaneously, their surface active properties also change, leading, for example in the case of suspensions or emulsions, to the collapse of the system.

We have found that the dicarboxylic acid hemiesters of alkylphenolpolyglycolethers of the general formula I,

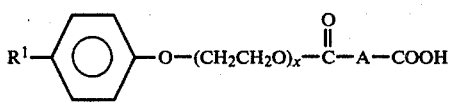  (I)

where
R$^1$ is a C$_{1-12}$ alkyl group;
A is —(CH$_2$)$_n$— (where n is 0-6); —CH=CH—; phenylene; or an alkylphenylene group (e.g. C$_{1-6}$alkylphenylene);
and
x is an integer of from 3 to 35;
and the salts of the above compounds formed with inorganic or organic bases, have outstanding surface active properties. They also show good tolerance to hard water since the carboxyl group on a strongly hydrophilic part of the compound ensures the water solubility of the calcium and magnesium salts.

The compounds of formula (I) can be manufactured by generally known methods, as follows:

(a) by reaction of an alkylphenolpolyglycolether of the general formula

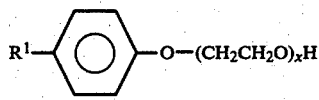

with a dicarboxylic acid anhydride of the general formula

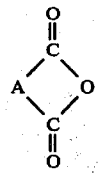

wherein R$^1$, A and X are as defined above. The reaction may be performed at elevated temperature, optionally in the presence of a solvent.

(b) instead of dicarboxylic acid anhydride as used in process (a), a dicarboxylic acid of the general formula HOOC—A—COOH may be used as the starting material. The reaction may again be performed at elevated temperature and the water formed in the process may be continuously removed by azeotropic or heterogenous distillation. When the water evolution ceases a hemiester of the general formula I is obtained.

(c) any reactive derivative of a dicarboxylic acid (such as an acid halide) of the general formula HOOC—A—COOH may also be used as the starting material in process (a), provided that it is capable of transforming the alkylphenolpolyglycolether into a hemiester of the general formula I.

We have also found that hemiester derivatives of succinic acid of the general formula II $$R^2-CH-CH_2-COOZ$$
$$|$$
$$COOH$$
(II)

where
R$^2$ is C$_8$-C$_{12}$ alkyl or alkenyl;
Z is —(CH$_2$CH$_2$O)$_x$—H of $$-(CH_2\overset{CH_3}{\underset{|}{C}}HO)_x-H;$$

and
x is as defined above,
and the salts of these compounds with inorganic or organic bases, possess excellent surface active properties and good tolerance to hard water.

These compounds can also be produced by generally known methods. For example, a dicarboxylic acid anhydride of the general formula $$R^2-CH-CH_2$$
$$\phantom{R^2-}O=C\quad C=O$$
$$\phantom{R^2-CH-}\backslash O /$$

may be reacted with a polyalkyleneglycol of the general formula HOZ. The two substances may be reacted together at elevated temperature, optionally in the presence of a solvent, to produce the hemiester of general formula II.

Examples of new surface active agents according to the invention, which may be produced by the above described methods, are as follows:

C$_9$H$_{19}$—⟨O⟩—O—(CH$_2$CH$_2$O)$_x$OC—A—COOH

| No. | A | x | Consistency | Acid no. mg KOH/g | HLB value |
|---|---|---|---|---|---|
| 1 | —CH=CH— | 9-10 | viscous | 75-80 | 11.5 |
| 2 | —CH=CH— | 11 | " | 70-75 | 11.5 |
| 3 | —CH=CH— | 13 | " | 60-65 | 12.5 |
| 4 | —CH=CH— | 23 | waxlike | 30-35 | 14.5 |
| 5 | o-phenylene | 9-10 | viscous | 72-77 | 10.5 |
| 6 | o-phenylene | 11 | " | 66-70 | 11.0 |
| 7 | o-phenylene | 13 | waxlike | 56-60 | 11.0 |

-continued

| No. | | | Consist-ency | Acid no. mg KOH/g | HLB value |
|---|---|---|---|---|---|
| 8 | o-phenylene | 23 | " | 30–35 | 12.5 |
| 9 | —CH$_2$—CH$_2$— | 9–10 | viscous | 75–80 | 11.0 |
| 10 | —CH$_2$—CH$_2$— | 11 | " | 70–75 | 11.5 |
| 11 | —CH$_2$—CH$_2$— | 13 | " | 60–65 | 12.0 |
| 12 | —CH$_2$—CH$_2$— | 23 | " | 30–35 | 14.0 |

$$R^2\text{—CH—CH}_2\text{—COOZ}$$
$$|$$
$$\text{COOH}$$

| No. | R$^2$ | Z | Consist-ency | Acid no. mg KOH/g | HLB value |
|---|---|---|---|---|---|
| 13 | n-nonenyl | —(CH$_2$CH$_2$O)$_{34}$—H | waxlike | 30–35 | 17.5 |
| 14 | n-dodecenyl | —(CH$_2$CH$_2$O)$_{34}$—H | " | 30–35 | 18.0 |
| 15 | nonenyl | —(CH$_2$CH$_2$O)$_9$—H | viscous | 100–110 | 15.0 |
| 16 | dodecenyl | —(CH$_2$CH$_2$O)$_9$—H | " | 100–110 | 15.0 |

It was found that the acidic strength of the surface active agents of the general formula I closely depends on the group A, as illustrated in the following table.

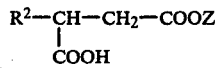—O(CH$_2$CH$_2$O)$_x$OC—A—COOH

| | | pH in distilled water | | |
|---|---|---|---|---|
| A | x | 1.0 g/l | 0.1 g/l | 0.01 g/l |
| —CH=CH— | 9–10 | 3.1 | 5.2 | 6.1 |
| —CH=CH— | 11 | 3.2 | 5.4 | 6.0 |
| —CH=CH— | 13 | 3.2 | 5.4 | 6.3 |
| o-phenylene | 9–10 | 3.45 | 5.7 | 6.6 |
| o-phenylene | 11 | 3.5 | 5.75 | 6.4 |
| o-phenylene | 13 | 3.6 | 5.6 | 6.5 |
| —CH$_2$—CH$_2$— | 9–10 | 4.85 | 5.85 | 6.5 |
| —CH$_2$—CH$_2$— | 11 | 4.7 | 5.8 | 6.3 |
| —CH$_2$—CH$_2$— | 13 | 4.9 | 5.85 | 6.4 |

It was found further that the acidic strength of the surface active agents of the general formula II according to the invention is influenced also—though to a substantially lower degree—by the group Z, as shown below by the following examples:

$$R^2\text{—CH—CH}_2\text{—COOZ}$$
$$|$$
$$\text{COOH}$$

| | | pH in distilled water | | |
|---|---|---|---|---|
| R$^2$ | Z | 1.0 g/l | 0.1 g/l | 0.01 g/l |
| n-nonenyl | —(CH$_2$CH$_2$O)$_{34}$—H | 3.8 | 4.2 | 4.9 |
| n-nonenyl | —(CH$_2$CH$_2$O)$_9$—H | 3.6 | 4.0 | 5.0 |

We have also surprisingly found that by the appropriate variation of the groups A and Z a whole series of surface active agents can be produced across the 3 to 6 pH range. The invention thus provides an extensive variety of hard water tolerant anionic surface active agents for many different applications.

We have also found that the new surface active agents, even at very low concentration, reduce the surface tension of water, as illustrated below:

C$_9$H$_{19}$—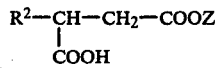O(CH$_2$CH$_2$O)$_x$OCACOOH

| A | x | Surface tension in distilled water 25° C., 1.0 g/l (dyn/cm) |
|---|---|---|
| —CH=CH— | 9–10 | 44.6 |
| —CH=CH— | 13 | 46.9 |
| o-phenylene | 9–10 | 44.3 |
| o-phenylene | 13 | 37.8 |
| —CH$_2$—CH$_2$— | 9–10 | 42.8 |
| —CH$_2$—CH$_2$— | 13 | 42.9 |

$$R^2\text{—CH—CH}_2\text{COOZ}$$
$$|$$
$$\text{COOH}$$

| R$^2$ | Z | Surface tension in distilled water 25° C., 1.0 g/l (dyn/cm) |
|---|---|---|
| n-nonenyl | —(CH$_2$CH$_2$O)$_{34}$—H | 54.7 |
| n-dodecenyl | —(CH$_2$CH$_2$O)$_{34}$—H | 40.9 |

The surface active agents according to the invention can be mixed with nonionic and anionic type surfactants and thus can advantageously be used with most common emulsifying mixtures, as the anionic component.

The use of the new surfactants is particularly advisable in products in which for some reason an acidic medium must be provided, e.g. in certain plant protective chemicals which after formulation must be stored in an acidic medium to prevent decomposition.

The salts of the surfactants of the invention with inorganic and organic bases can be utilised in all fields where other anionic surface active agents are used.

The invention is illustrated by the following examples.

EXAMPLE 1

200 g nonylphenolpolyglycolether (x=9–10, OH: 86–90 mg KOH/g) and 25.0 g maleic acid anhydride are warmed up to 70° C. with constant mixing and kept at this temperature for one hour. Cooled down to room temperature, the mixture yields the desired surface active agent. Acid no.: 75–80 KOH/g, HLB: 11.5.

EXAMPLE 2

390 g nonylphenolpolyglycolether (x=13, OH: 70–72 mg KOH/g) and 49 g maleic acid anhydride are warmed up to 70° C. with mixing and kept at this temperature for one hour. Cooled down to room temperature, the mixture yields the desired surface active agent. Acid no.: 60–65 mg KOH/g, HLB: 12.5.

EXAMPLE 3

200 g nonylphenolpolyglycolether (x=9-10, OH: 86-90 mg KOH/g) and 26 g succinic acid anhydride are warmed up to 90° C. with mixing and kept at this temperature for one hour. Cooled down to room temperature, the mixture yields the desired surface active agent. Acid no.: 75-80 mg KOH/g, HLB: 11.0.

EXAMPLE 4

200 g nonylphenolpolyglycolether (x=9-10, OH: 86-90 mg KOH/g) and 38.0 g phthalic acid anhydride are warmed up to 90° C. with mixing and kept at this temperature for one hour. Cooled down to room temperature, the mixture yields the desired surface active agent. Acid no.: 75-80 mg KOH/g, HLB: 10.5.

EXAMPLE 5

490 g nonylphenolpolyglycolether (x=13, OH: 70-72 mg KOH/g) and 50 g succinic acid anhydride are warmed up to 90° C. with mixing and kept at this temperature for one hour. Cooled down to room temperature, the mixture yields the desired surface active agent. Acid no.: 58-63 mg KOH/g, HLB: 12.0.

EXAMPLE 6

500 g nonylphenolpolyglycolether (x=23, OH: 50-55 mg KOH/g) and 45 g maleic acid anhydride are caused to react in 190 g xylene at 70° C. for one hour. Cooled down to room temperature, the mixture yields the desired surface active agent. Acid no.: 35-40 mg KOH/g, HLB: 16.2, non-volatile matter: 75%.

EXAMPLE 7

200 g nonylphenolpolyglycolether (x=9-10, OH: 86-90 mg KOH/g) and 38.0 g phthalic acid are made to react in 35 g xylene at a temperature of 160° C. The water produced is distilled off with xylene. In 3 to 4 hours, when no more water is formed, xylene is distilled off from the mixture. Cooled down to room temperature, the desired surface active agent is obtained. Acid no.: 75-80 mg KOH/g, HLB: 10.5.

EXAMPLE 8

22.4 g nonenyl-succinic acid anhydride is warmed up to 90° C. with constant mixing. 150.0 g polyethylene glycol 1500 (x=34) is added to it in drops over 30 minutes, then stirred for a full hour at a temperature of 90° C. Cooled down it yields the desired surface active agent. Acid no.: 31.5 mg KOH/g, HLB: 15.0.

EXAMPLE 9

144 g butylphenolpolyglycolether (x=13, OH: 76-78 mg KOH/g) and 20 g succinic acid anhydride are reacted at 90° C. for one hour. Cooled down to room temperature, the mixture yields the desired surface active agent. Acid no.: 66-70 mg KOH/g, HLB: 13.

EXAMPLE 10

167 g dodecylpolyglycolether (x=13, OH: 66-69 mg KOH/g) and 20 g succinic acid anhydride are reacted at 90° C. for one hour. Cooled down to room temperature, the mixture yields the desired surface active agent. Acid no.: 59-61 mg KOH/g, HLB: 12.

EXAMPLE 11

22.4 g nonenyl-succinic acid anhydride is warmed up to 90° C. with constant mixing. 29.0 polyethylene glycol 300 (x=7) is added to it in drops over 30 minutes, and the mixture is stirred for a full hour at a temperature of 90° C. Cooled down, it yields the desired surface active agent. Acid no.: 106-109 mg KOH/g, HLB: 10.5.

EXAMPLE 12

This is an example of the use of the surface active agents of invention. Parts are by weight.

A mixture is produced of
- 8 parts 2-(methoxycarbonylamino)-phenyl-N-(m-tolyl)-carbamate,
- 8 parts 2-(ethoxycarbonylamino)-phenyl-(N-phenyl)-carbamate,
- 20 parts cyclohexanone
- 10 parts isophorone
- 30 parts xylene
- 10 parts nonylphenol-polyglycolether
- 10 parts nonylphenol-polyglycolether-maleic acid hemiester.
- 4 parts calcium phenylsulfonate and stored for 20 days at 40, 50 and 60° C. respectively in parallel with a standard product. After the storage period the quantity of decomposed active ingredient was measured.

The results are shown in the following table:

| Sample | Decomposed active ingredient in %, at | | |
|---|---|---|---|
| | 40° C. | 50° C. | 60° C. |
| Above example | <1 | <1 | <2 |
| Standard product | <1 | <1 | <5 |

The biological effectiveness of the product was equal to that of the standard.

We claim:

1. Anionic surface active agents of the formula

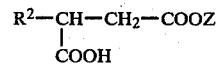

where
$R^2$ is $C_{8-12}$ alkyl or alkenyl; and
Z is $-(CH_2-CH_2-O)_x-H$ or

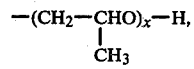

wherein x is an integer of 3 to 35 and the salts with inorganic and organic bases.

2. Surface active agents as claimed in claim 1 in which $R^2$ is nonenyl or dodecenyl.